United States Patent [19]

Durkee et al.

[11] Patent Number: 4,697,601
[45] Date of Patent: Oct. 6, 1987

[54] TONGUE FORCE MEASURING DEVICE

[76] Inventors: Darryl L. Durkee, 449 W. Glenoaks Blvd., Glendale, Calif. 91202; Frank E. Manning, 2716 Cumbers Rd., #8, Valley Center, Calif. 92082

[21] Appl. No.: 940,933
[22] Filed: Dec. 12, 1986
[51] Int. Cl.$^4$ ............................................. A61B 5/10
[52] U.S. Cl. ........................................ 128/777; 73/379; 73/862.04
[58] Field of Search ................ 128/777, 774; 434/185; 73/379, 862.04

[56] References Cited

U.S. PATENT DOCUMENTS

| | | | |
|---|---|---|---|
| 3,800,782 | 4/1974 | Josephson et al. | 128/777 |
| 4,501,148 | 2/1985 | Nicholas et al. | 173/379 |
| 4,585,012 | 4/1986 | Rumburg | 128/777 |

Primary Examiner—Kyle L. Howell
Assistant Examiner—John C. Hanley
Attorney, Agent, or Firm—Frank D. Gilliam

[57] ABSTRACT

A device for measuring forces generated by a human tongue in three dimensions, i.e., along X, Y and Z axis. The device comprises a housing having sidewalls (preferably cylindrical), a closed back wall and a front wall having a central opening. An elongated beam extend through the opening into the housing to a mounting member which secures the inner beam end to the housing near the back wall. Strain gages are mounted on the beam near the mounting member to measure deflection of the free beam end in X and Y directions. A diaphragm extends across the housing between the mounting member and the back wall. A pin is movably positioned in a axial bore in the beam with one end in contact with the diaphragm and the other extending beyond the beam and housing. Strain gages mounted on the diaphragm detect movement of the diaphragm in the Z direction in response to changing force of the pin against the diaphragm. A tongue cup is mounted on the free end of the pin to receive a patient's tongue when the cup is inserted between the teeth. A tooth plate fastened to the housing adjacent to the opening is gripped between the patient's teeth to hold the tongue cup in position. Signals generated by the strain gages can be monitored on a meter, oscilloscope or computer display as the patient moves the tongue, pronounces words, etc. The results, when compared between a person having normal speech and one having speech disorders, are useful in diagnosing and treating the disorders.

14 Claims, 9 Drawing Figures

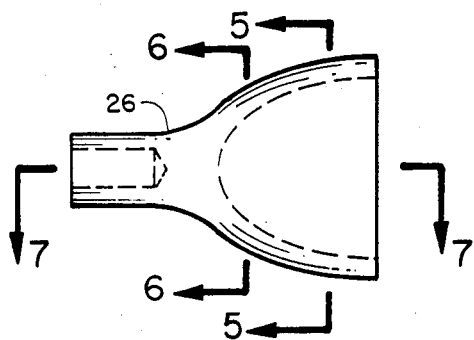
FIGURE 4
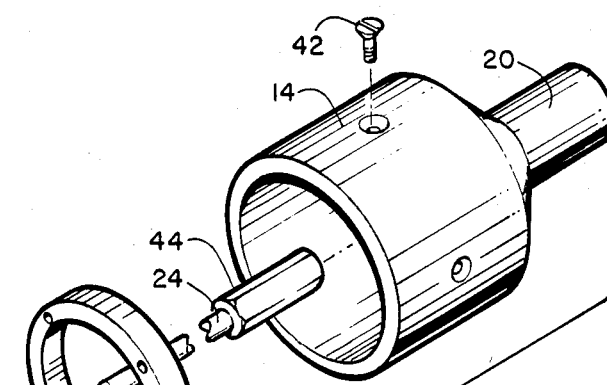
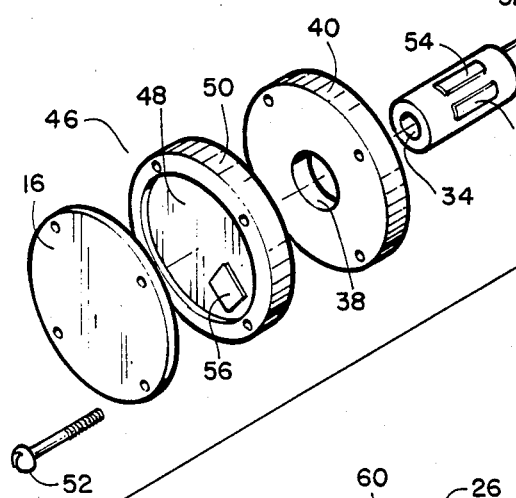
FIGURE 3
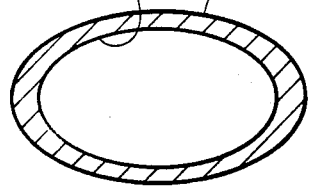
FIGURE 6
FIGURE 7
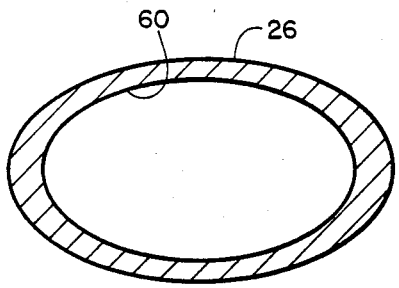
FIGURE 5
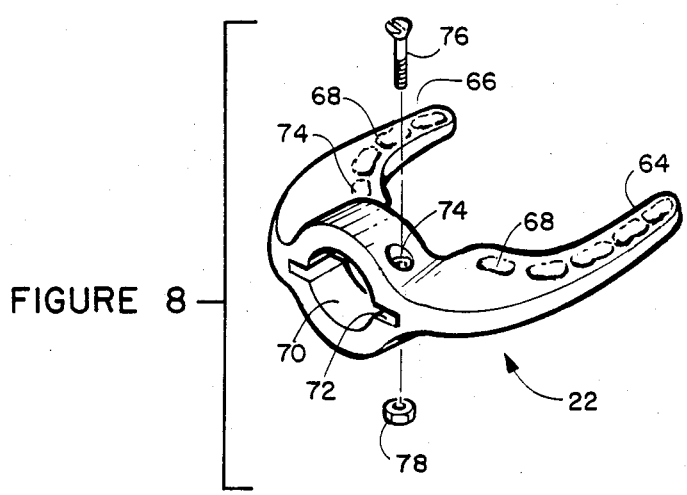
FIGURE 8

4,697,601

TONGUE FORCE MEASURING DEVICE

BACKGROUND OF THE INVENTION

This invention relates in general to speech diagnosis therapy and, more specifically, to a tongue force measuring device for use in speech therapy.

Some speech pathologists feel that certain speech disorders stem from poor tongue strength in one or more directions of tongue movement. Treatment of the problem is usually attempted when the subject is a child. Attempts have been made to measure tongue strength using a load cell placed toward the middle of the tongue with the head restrained. Since the cell measured only mid-tongue strength in a single direction, the results were of limited value. This work was described by J. P. Working et al. in their article "Tongue Strength Part I: Following Total Laryngectomy" *The Laryngoscope*, 90 (1980), pp. 680-684. Other attempts to measure tongue strength use head restraints and cumbersome equipment which tend to frighten small children, detracting from validity of results.

A number of devices have been developed to detect linguapalatal contact during phonation by means of a pattern of spaced electrical contacts on an artificial palate. Typical of these are the devices described by Takinishi et al. in U.S. Pat. No. 4,310,002, Fletcher et al. in U.S. Pat. No. 4,112,596 and Hori in U.S. Pat. No. 4,287,895. While these provide information as to tongue location during speech which is useful in treating speech disorders, they provide no information on tongue strength or force in any particular direction during speech.

An oral strain gage is described by Davis et al. in U.S. Pat. No. 3,297,021. However, this device measures only pressure between the jaws during chewing or the like. Since the strain gage is embedded in an artificial tooth, it is incapable of measuring tongue force.

Thus, there is a continuing need for a device for measuring tongue force during speech in three dimensions while simultaneously being light, compact and suitable for use by children.

SUMMARY OF THE INVENTION

The above-noted problems, and others, are overcome by the tongue force measuring device of this invention which, basically, comprises beam mounted strain gages to measure forces in X and Y directions as the beam is deflected by tongue movement and diaphragm mounted strain gages to measure tongue force in the Z (tongue thrust) direction. Forces in intermediate directions can be determined from combinations of forces in the three basic directions.

The device is contained within a housing having side walls (which can form a circular, square, hexagonal, etc. housing cross-section), a closed back wall and a front wall having an opening therein. A beam extends into the housing through the opening to a beam mounting means which secures the beam to the housing near the back wall. A diaphragm extends across the housing between the sidewalls between the back wall and the beam mounting means. A pin extends through an axial bore through the beam, with one pin end in contact with the diaphragm and the free end extending beyond the free end of the beam. The pin includes means to prevent rotation of the pin relative to the beam, such as cooperating spline means on the two components. A tongue cup is secured to the free end of the pin and has a cup like hollow on the opposite end adapted to receive the end of the patient's tongue.

A tooth plate similar to a conventional dental impression plate is fastened to the front wall near the opening (preferably, a short tubular extension of the front wall) and extends between the patient's teeth. The patient grips the plate with his teeth with his tongue in the tongue cup. As the tongue is moved in speaking or the like, the tongue applies forces to the tongue cup in different directions, deflecting the beam and varying the pin force on the diaphragm.

In order to detect and measure the varying forces, at least two (preferably four) strain gages are mounted on the beam within the housing at 90° to each other and at least one (preferably two) strain gages are mounted on the diaphragm. The signals from the strain gages are directed to an amplifying bridge circuit and then to any conventional output device such as meters, oscilloscopes or computer displays.

Results obtained by comparing tongue forces of persons having normal speech with those having speech disorders but of similar age, sex, native language, etc. will be helpful in analyzing problems, prescribing treatment, determining tongue exercises, etc., for those having speech disorders.

BRIEF DESCRIPTION OF THE DRAWING

Details of the invention and of preferred embodiments thereof will be further understood upon reference to the drawing wherein:

FIG. 3 is an exploded perspective view showing the internal components of the device;

FIG. 4 is a plan view of the tongue cup;

FIG. 5 is a section view through the tongue cup taken on line 5—5 in FIG. 4;

FIG. 6 is a section view through the tongue cup taken on line 6—6 in FIG. 4;

FIG. 7 is a section view through the tongue cup taken on line 7—7 in FIG. 4;

FIG. 8 is a perspective view of the tooth plate; and

DETAILED DESCRIPTION OF THE INVENTION

Figure 1:
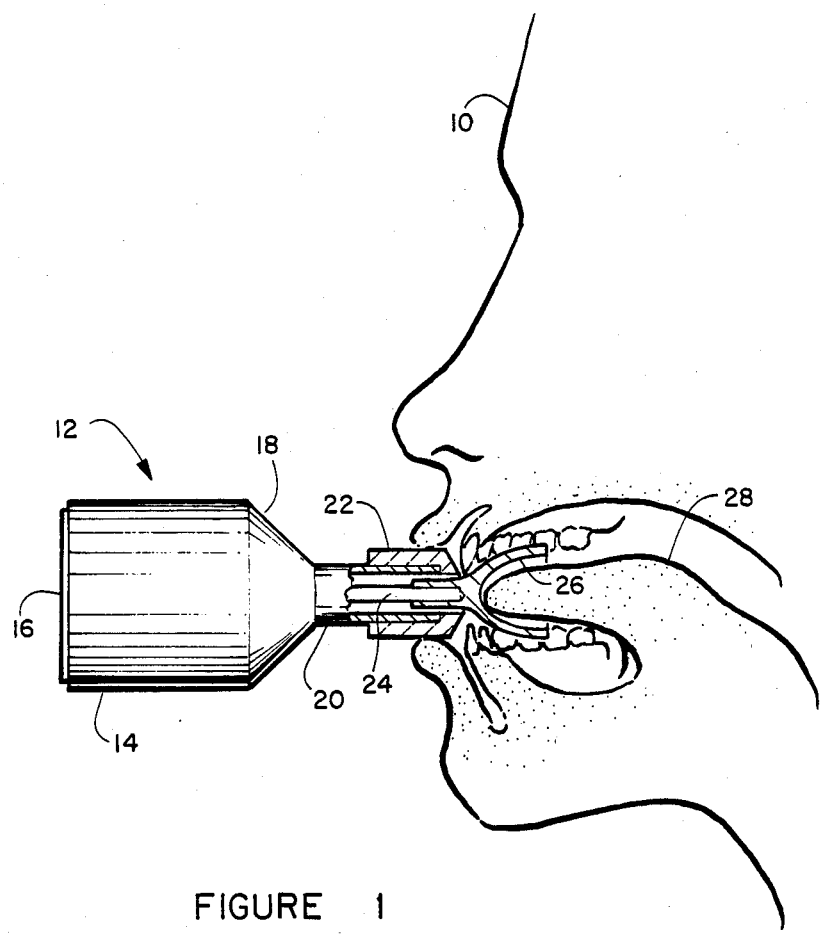
FIG. 1 is an elevation view, partially cut away, showing the tongue force measuring device in use by a person.

Referring now to FIG. 1, there is seen a patient 10 using the tongue force measuring device 12 to measure tongue forces in three dimensions. The device housing comprises side walls 14 (here, cylindrical sidewalls), a closed back wall 16 and a front wall 18, here frustoconical in configuration with a short tubular extension 20. The teeth of patient 10 grip a tooth plate 22, fastened to tubular extension 20. Tooth plate 22 is mostly not shown in FIG. 1 but is detailed in FIG. 8 and described below. A pin 24 extends outwardly of extension 20 and carries a tongue cup 26 on its free end. The patient's tongue 28 extends into tongue cup 26 (detailed in FIGS. 4-7) and substantially fills the hollow end of the cup. As can be seen, when the patient 10 extends his tongue, cup 26 will be pressed into the housing of device 12 while upward or sideways movement of tongue 28 will press cup 26 in those directions.

Figure 2:
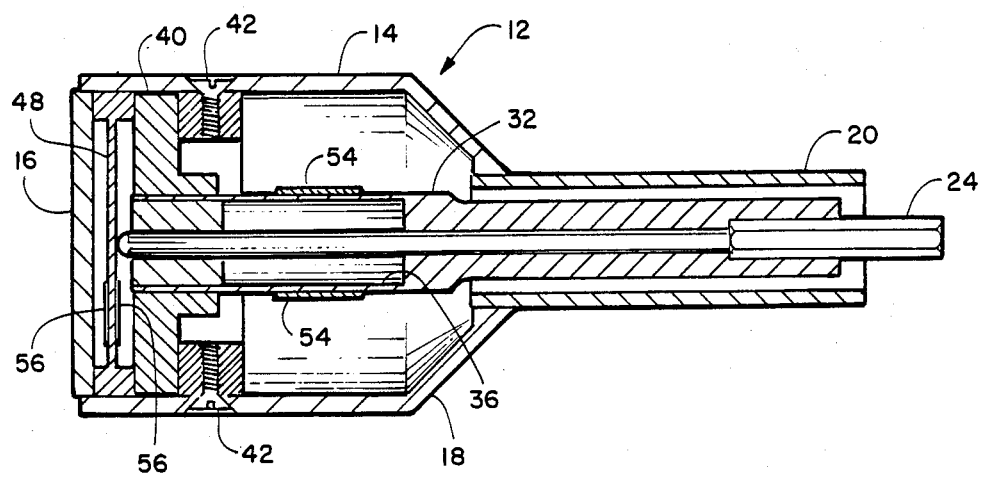
FIG. 2 is a horizontal section through the device, taken approximately on line 2—2 in FIG. 1.

Details of the internal components of the device 12 will be further understood upon reference to FIGS. 2 and 3, which show section and exploded views, respectively.

Beam 32 is an elongated rod having an axial opening or bore 34 and an enlarged open area 36 near one end. Most conveniently, beam 32 is fabricated by connecting two bored rods with a short section of tubing by soldering or the like. The innermost end of beam 32 is secured in a hold 38 in a disk 40 in any convenient manner, such as by solder, glue, or the like. Disk 40 abuts a ring 41 which is secured to sidewalls 14 by a plurality of screws 42. A portion of bore 34 near the free end of beam 32 has a non-round cross-section, such as splines or a hexagonal shape to receive a correspondingly shaped end portion 44 of pin 24 to prevent relative rotation of pin and beam while allowing pin 24 to easily slide axially within bore 34.

A metal disk 46 having a thin central diaphragm area 48 and a thick rim 50 is sized to fit snuggly within sidewalls 14 adjacent to beam mounting disk 40. The back wall 16 of the device consists of a disk which is held in place by a plurality of screws 52 which extend through wall 16, rim 50 and disk 40 and into holes in ring 41. These screws hold the assembly together and prevent rotation of diaphragm 48 and disk 40.

At least one strain gage 54 is mounted on the top of beam 32 at right angles to at least one strain gage 55 at the side of beam 32. Four equally spaced strain gages 54 and 55 are preferred for greater system accuracy and sensitivity, as further detailed below. The hollow portion of beam 32 behind strain gages 54 and 55 increases strain gage sensitivity. Suitable wires, not shown, extend from these strain gages through holes in side walls 14 to outside instrumentation.

At least one strain gage 56 is mounted on diaphragm 48. For best results, pairs of strain gages 56 are used as shown, with the gages of each pair on opposite sides of diaphragm 48 so that one is in compression and the other is in tension. This arrangement provides maximum sensitivity and accuracy, cancelling out any system errors.

Details of the tongue cup 26 are illustrated in FIGS. 4–7. While aluminum is preferred for other components of the device for light weight, resistance to corrosion and heat sterilizability, a high temperature resistant plastic such as a polyimide or an acetal resin such as that sold under the Delrin trademark by DuPont is preferred for tongue cup 26 since aluminum may have an objectionable taste to the user.

As seen in FIGS. 4–7, tongue cup 26 has a horizontally oriented generally oval or elliptical hollow 60 at one end sized to receive the patient's tongue. Several different sizes of tongue cups may be provided to accommodate different tongue sizes, if desired, although most tongues are quite adaptable to hollow size and shape. Opposite hollow 60 cup 26 has an axial bore 62 adapted to fit over and be secured to the free end of rod 24. Tongue cup 26 may be permanently or releasably secured in place, as desired, with any suitable fastening means such as glue, set screws or merely a snug friction fit.

While device 12 may be held in place by any suitable means, we prefer to use a tooth plate such as is shown in FIG. 8. Basically, tooth plate 22 is similar to a conventional dentist's impression plate, being a Delrin or an aluminum plate having legs 64 and 66 shaped to fit between the teeth with a layer of quick setting impression material such as Coltoflax from Coltene on the upper and lower surfaces of legs 64 and 66. The material is placed on the plate, which is inserted in the mouth and the patient bites down while the material sets. The plate and entire device 12 may then be removed and reinserted to exactly the same position. Plate 22 serves to establish device position and to separate the teeth a distance equal to the normal separation during speech. As seen in FIG. 8, the impressions 68 of the patient's teeth are visible. Line 69 schematically indicates the tooth line.

Tooth plate 22 has a large bore 70 adapted to slip over the free end of housing extension 20. Slots 72 are located on opposite sides of bore 70 and have holes 74 therethrough to receive bolts 76 and nuts 78 which can be tightened to clamp bore 70 onto extension 20 to firmly hold the tooth plate in place.

Figure 9:
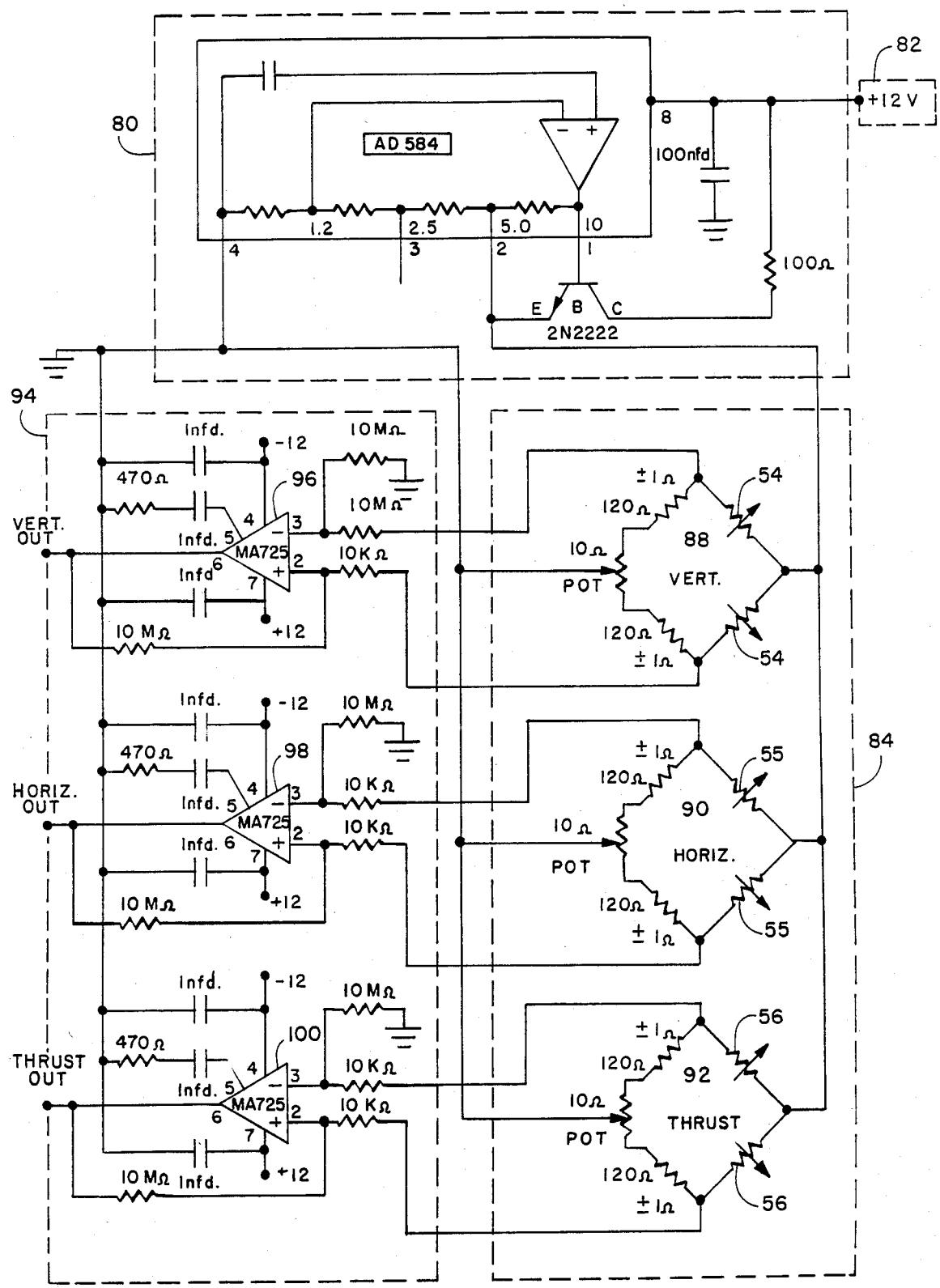
FIG. 9 is a schematic diagram of the strain gage bridge circuit.

FIG. 9 provides a typical schematic diagram for the system. The system is made up basically of three functional components of sub-circuits, namely a conventional voltage stabilization circuit 80 which receives current from a conventional power supply 82 and directs output to the Weatstone bridge array 84, then to amplification array 94 and finally to any suitable means for measuring and comparing output, such as meters, oscilloscope systems, computer display systems or the like.

First Wheatstone bridge 88 includes the top and bottom strain gages 54 on beam 32 which act as variable resistances. Second Wheatstone bridge 90 includes the two strain gages 55 on the sides of beam 32. Third Wheatstone bridge 92 includes the two strain gages 56 located on opposite sides of diaphragm 48. While single strain gages 54, 55 or 56 could be used in a bridge circuit instead of the pairs of opposed gages, the pairs of gages are strongly preferred because they double the sensitivity of the circuit and eliminate variations due to temperature changes that might cause excessive error. In our arrangement, each pair consists of one gage in tension and one gage in compression to assure maximum sensitivity and consistent readings.

The output of the bridge array passes to amplifier array 94. The output from bridge 88 passes to operational amplifier (op amp) 96, that from bridge 90 to op amp 98 and from bridge 92 to op amp 100.

Finally, the vertical, horizontal and thrust outputs can be measured and/or displayed by any suitable device, such as a meter, oscilloscope or computer display. We have found that the output of the system varies in a very linear manner with changes in force, making the output especially suitable for oscilloscope or computer displays.

The device can easily be calibrated by mounting the housing in a rotatable vice and hanging known weights from the tongue cup and noting the meter or oscilloscope reading. With our preferred system we have obtained voltages varying from plus 5 to minus five volts with weight variations from 5 pounds force (lbf) up to 5 lbf down. Thrust varies 5 volts with thrust forces of up to 5 lbf. Retraction forces are not measured. The system automatically measures forces in all skew directions except retraction.

Comparisons may be made between tongue forces generated between persons having normal speech and those having speech disorders. Measurements may be made of "normal" readings obtained when a person of similar sex, age and native language speaks selected words. These readings can then be compared to those obtained with a patient. Since the outputs from the load cells are substantially linear, conversion from analog to digital signals is simple, permitting convenient computer processing and display on a video monitor. Results from the video display aids speech therapists in diagnosis of speech problems and in evaluating progress of therapy for patients.

Other variations, applications and ramifications of this invention will occur to those skilled in the art upon reading this disclosure. Those are intended to be included.

We claim:

1. A device for measuring tongue forces in three dimensions which comprises:
   a substantially closed housing having an opening in one wall;
   an elongated beam extending into said housing through said opening and having a fixed end secured within said housing;
   a diaphragm within said housing adjacent to said fixed beam end;
   an axial bore through the length of said beam;
   a pin means extending through said bore for axial movement therein;
   means for preventing relative rotation between said pin and beam;
   said pin having one end adapted to contact said diaphragm and a free end extending beyond said beam;
   strain gage means on said beam for sensing beam bending;
   strain gage means on said diaphragm for sensing diaphragm deflection;
   tongue cup means fastened to said pin free end;
   said tongue cup having a hollow adapted to receive patients's tongue; and
   means for converting variations in strain in said strain gages caused by movement of a tongue against said tongue cup into proportional voltages.

2. The device according to claim 1 wherein said strain gage means on said beam comprises four strain gages equally spaced around the beam and said strain gage means on said diaphragm comprises two strain gages on opposite sides of said disphragm.

3. The device according to claim 2 wherein said beam is substantially hollow in the vicinity of said strain gages.

4. The device according to claim 1 further including a bifurcated tooth plate fastened to said housing adjacent to said opening, the legs of said tooth plate formed to fit between the teeth of the patient when the tongue cup is positioned against the tongue.

5. The device according to claim 4 further including a layer of dental impression material on at least one surface of said plate adapted to be pressed against the teeth when a patient bites against the plate.

6. A device for measuring tongue forces in three dimensions which comprises:
   a housing having a closed back wall, closed side walls; and a front wall having an opening therein;
   an elongated beam extending into said housing through said opening;
   a beam mounting means securing the innermost end of said beam to said housing;
   a diaphragm extending between said sidewalls between said beam mounting means and said back wall;
   an axial bore through the length of said beam;
   a pin positioned within said bore for axial movement therein;
   cooperating means on said pin and bore for preventing relative rotation therebetween;
   one end of said pin adapted to contact said diaphragm while the opposite end of said pin extends beyond said beam;
   a tongue cup secured to the extended end of said pin and having a hollow opposite said pin adapted to accept the end portion of a patient's tongue;
   at least two strain gages secured to said beam within said housing;
   said strain gages lying at angles of about 90° to each other;
   at least one strain gage attached to a surface of said diagram; and
   means for obtaining electrical signals corresponding to varying strain in said strain gages.

7. The device according to claim 6 wherein four strain gages are attached to said beam.

8. The device according to claim 7 wherein said beam is substantially hollow in the region of said strain gages.

9. The device according to claim 6 wherein two strain gages are attached to opposite sides of said diaphragm.

10. The device according to claim 6 further including a tooth plate secured to said front wall adjacent to said opening and having two legs extending around said tongue cup adapted to substantially align with a patient's teeth when the patient's tongue is in said tongue cup whereby a patient can support the device by gripping the tooth plate with his teeth and the tooth plate maintains the proper tooth separation for speaking.

11. The device according to claim 10 further including a layer of dental impression material on the upper and lower surfaces of said tooth plate to aid in uniform replacement position when the device is removed and replaced in a patient's mouth.

12. The device according to claim 10 further including a short tubular extension of said front wall around said opening and means to removably clamp said tooth plate to said extension.

13. The device according to claim 6 wherein four strain gages are provided evenly spaced around said beam and two strain gages are provided on opposite sides of said diaphragm and said means for obtaining electrical signals includes a power supply, a voltage stabilization circuit, Wheatstone bridge circuits for converting varying resistance in said strain gages to varying voltages and amplifier circuits to amplify the bridge signals and wherein each pair of opposed strain gages act as varying resistances in two legs of each Wheatstone bridge.

14. the device according to claim 6 wherein all of the structural components of said device are formed from aluminum except said tongue cup and tooth plate which are formed from corrosion resistant metal or a high temperature resistant plastic.

* * * * *